(12) United States Patent
Wang et al.

(10) Patent No.: US 9,783,558 B2
(45) Date of Patent: *Oct. 10, 2017

(54) COMPOSITION AND METHOD FOR LOW TEMPERATURE CHEMICAL VAPOR DEPOSITION OF SILICON-CONTAINING FILMS INCLUDING SILICON CARBONITRIDE AND SILICON OXYCARBONITRIDE FILMS

(71) Applicant: Entegris, Inc., Billerica, MA (US)

(72) Inventors: Ziyun Wang, Allen, TX (US); Chongying Xu, Suzhou (CN); Bryan Hendrix, Danbury, CT (US); Jeffrey Roeder, Brookfield, CT (US); Tianniu Chen, Westford, MA (US); Thomas H. Baum, New Fairfield, CT (US)

(73) Assignee: Entegris, Inc., Billerica, MA (US)

( * ) Notice: Subject to any disclaimer, the term of this patent is extended or adjusted under 35 U.S.C. 154(b) by 267 days.

This patent is subject to a terminal disclaimer.

(21) Appl. No.: 14/798,775

(22) Filed: Jul. 14, 2015

(65) Prior Publication Data

US 2015/0315215 A1    Nov. 5, 2015

Related U.S. Application Data

(63) Continuation of application No. 14/333,536, filed on Jul. 17, 2014, now Pat. No. 9,102,693, which is a continuation of application No. 12/862,739, filed on Aug. 24, 2010, now Pat. No. 8,802,882, which is a continuation of application No. 12/578,262, filed on Oct. 13, 2009, now Pat. No. 7,781,605, which is a continuation of application No. 10/870,106, filed on Jun. 17, 2004, now Pat. No. 7,601,860, which is a continuation-in-part of application No. 10/683,501, filed on Oct. 10, 2003, now Pat. No. 7,579,496.

(51) Int. Cl.
C07F 7/10 (2006.01)
H01L 21/02 (2006.01)

(52) U.S. Cl.
CPC .......... *C07F 7/10* (2013.01); *H01L 21/02271* (2013.01)

(58) Field of Classification Search
CPC ....................................................... C07F 7/10
USPC ....................................................... 556/410
See application file for complete search history.

(56) References Cited

U.S. PATENT DOCUMENTS

| | | |
|---|---|---|
| 5,204,141 A | 4/1993 | Roberts et al. |
| 5,424,095 A | 6/1995 | Clark et al. |
| 5,578,530 A | 11/1996 | Muroyama et al. |
| 5,744,196 A | 4/1998 | Laxman et al. |
| 5,939,333 A | 8/1999 | Hurley et al. |
| 5,990,541 A | 11/1999 | Saito et al. |
| 6,013,235 A | 1/2000 | Brinson et al. |
| 6,383,955 B1 | 5/2002 | Matsuki et al. |
| 6,410,463 B1 | 6/2002 | Matsuki |
| 6,936,548 B2 | 8/2005 | Dussarrat et al. |
| 7,019,159 B2 | 3/2006 | Dussarrat et al. |
| 7,064,083 B2 | 6/2006 | Dussarrat et al. |
| 7,132,723 B2 | 11/2006 | Park et al. |
| 7,172,792 B2 | 2/2007 | Wang et al. |
| 7,446,217 B2 | 11/2008 | Wang et al. |
| 7,531,679 B2 | 5/2009 | Wang et al. |
| 7,579,496 B2 | 8/2009 | Wang et al. |
| 7,601,860 B2 | 10/2009 | Wang et al. |
| 7,713,346 B2 | 5/2010 | Wang et al. |
| 7,781,605 B2 | 8/2010 | Wang et al. |
| 7,786,320 B2 | 8/2010 | Wang et al. |
| 7,863,203 B2 | 1/2011 | Wang et al. |
| 7,887,883 B2 | 2/2011 | Wang et al. |
| 7,910,765 B2 | 3/2011 | Wang et al. |
| 8,242,032 B2 | 8/2012 | Wang et al. |
| 8,541,318 B2 | 9/2013 | Wang et al. |
| 8,802,882 B2 | 8/2014 | Wang et al. |
| 9,102,693 B2 * | 8/2015 | Wang ................ H01L 21/02271 |
| 2001/0048973 A1 | 12/2001 | Sato et al. |
| 2003/0129826 A1 | 7/2003 | Werkhoven et al. |
| 2004/0096582 A1 | 5/2004 | Wang et al. |
| 2004/0121085 A1 | 6/2004 | Wang et al. |
| 2004/0138489 A1 | 7/2004 | Wang et al. |
| 2004/0146644 A1 | 7/2004 | Xiao et al. |
| 2004/0194706 A1 | 10/2004 | Wang et al. |
| 2005/0009320 A1 | 1/2005 | Goundar |
| 2005/0080285 A1 | 4/2005 | Wang et al. |

(Continued)

FOREIGN PATENT DOCUMENTS

| | | |
|---|---|---|
| EP | 0521772 A1 | 1/1993 |
| EP | 1441042 A1 | 7/2004 |

(Continued)

OTHER PUBLICATIONS

Chen, L., et al., "Crystalline silicon carbon nitride: A wide band gap semiconductor", "Appl. Phys. Letters.", May 11, 1998, pp. 2463-2465, vol. 72, No. 19.
Denk, M., et al., "Synthesis and Structure of a Stable Silylene", "J. Am. Chem. Soc.", Mar. 23, 1994, pp. 2691-2692, vol. 116, No. 6.
Drost, C., et al., "Erste Fluorfunktionelle Silylhydrazin-Sechsringe", "Journal of Organometalic Chemistry", Aug. 27, 1991, pp. 307-310 (English Abstract), vol. 414.
Gibson, G., et al., "The Reaction of Silicon Tetrachloride with N,N-Dimethylhydrazine and Hydrazine", "Inorg. Chem.", Aug. 1963, pp. 876-878, vol. 2, No. 4.
Haaf, M., et al., "Synthesis and Reactivity of the Stable Silylene N,N'-Di-Tert-Butyl-1,3-Diaza-2-Sila-2-Ylidene", "Canadian Journal of Chemistry", Nov. 2000, pp. 1526-1533 (Abstract), vol. 78, No. 11.

(Continued)

*Primary Examiner* — Sudhakar Katakam
*Assistant Examiner* — Kofi Adzamli

(57) ABSTRACT

Silicon precursors for forming silicon-containing films in the manufacture of semiconductor devices, such as films including silicon carbonitride, silicon oxycarbonitride, and silicon nitride ($Si_3N_4$), and a method of depositing the silicon precursors on substrates using low temperature (e.g., <550° C.) chemical vapor deposition processes, for fabrication of ULSI devices and device structures.

20 Claims, 1 Drawing Sheet

(56) References Cited

U.S. PATENT DOCUMENTS

| | | |
|---|---|---|
| 2005/0080286 A1 | 4/2005 | Wang et al. |
| 2008/0160174 A1 | 7/2008 | Wang et al. |
| 2009/0084288 A1 | 4/2009 | Wang et al. |
| 2010/0068894 A1 | 3/2010 | Wang et al. |
| 2010/0314590 A1 | 12/2010 | Wang et al. |
| 2011/0136343 A1 | 6/2011 | Wang et al. |
| 2011/0165762 A1 | 7/2011 | Wang et al. |
| 2011/0183528 A1 | 7/2011 | Wang et al. |
| 2012/0156894 A1 | 6/2012 | Wang et al. |
| 2012/0178267 A1 | 7/2012 | Wang et al. |

FOREIGN PATENT DOCUMENTS

| | | |
|---|---|---|
| EP | 1149934 B1 | 8/2005 |
| FR | 2693204 A1 | 1/1994 |
| JP | 08-22986 A | 1/1996 |
| JP | 2000-80476 A | 3/2000 |
| WO | 03046253 A1 | 6/2003 |

OTHER PUBLICATIONS

Heinicke, J., et al., "Aminosubstituted disilanes: Synthesis by unsymmetrical and symmetrical reductive coupling", "Heteroatom Chem.", 1998, pp. 311-316, vol. 9, No. 3.

Hoefler, F., et al., "Uber die Trimethylsilylderivate des Methylhydrazins. Trimethyl-trimethylsilyl-hydrazin", "Monatshefte fur Chemie und verwandte Teile anderer Wissenshaften", Nov. 1966, pp. 1598-1610, vol. 97.

Hoefler, F., et al., "Uber die Trimethylsilylderivate des Methylhydrazins. Trimethyl-trimethylsilyl-hydrazin", "Monatshefte fur Chemie und verwandte Teile anderer Wissenshaften", Nov. 1966, pp. 1598-1610 (English Abstract), vol. 97.

Huppmann, F., et al., "Reaktionen subvalenter Verbindungen des Siliciums mit alkylierten Aromaten", "Journal of Organometallic Chemistry", 1994, pp. 217-228 (English Abstract), vol. 483.

Lee, G., et al., "Bis[bis(trimethylsilyl)amino]silylene, an Unstable Divalent Silicon Compound", "J. Am. Chem. Soc.", Jul. 9, 2003, pp. 8114-8115, vol. 125, No. 27.

Mitzel, N., "Simple silylhydrazines as models for Si—N beta-donor interactions in SiNN units", "Chem. Eur. J.", 1998, pp. 692-698, vol. 4, No. 4.

Rakhlin, V., et al., "Organosilicon Derivatives of 1,1-Dimethylhydrazine: Novel Precursors of Thin-Film Dielectric Coatings", "Doklady Chemistry", Feb. 2003, pp. 47-49, vol. 388, No. 4-6.

Scherer, O., et al., "Chemical Abstract 1965:439205, Ethylenimine and imidazolidinone derivatives of silicon", "Chemische Berichte", 1965, pp. 2243-2247, vol. 98, No. 7.

Schuh, H., et al., "Disilanyl-Amines-Compounds Comprising the Structural Unit Si—Si—N, as Single Source Precursors for Plasma-Enhanced Chemical Vapour Deposition (PE-CVD) of Silicon Nitride", "Z. anorg. allg. Chem.", 1993, pp. 1347-1352 (English Abstract), vol. 619.

Sergeeva, Z., et al., "Chemical Abstract 1959:62140; Synthesis of 1,1-dialkyl-2-(trialkylsilyl)hydrazines", "Khim. i Prakt. Primenenie Kremneorg. Soedinenii", 1958, pp. 235-241, vol. 1.

Sergeeva, Z., et al., "Chemical Abstract 1960:127948, Synthesis of alkyl- and dialkylbis(1,1-dialkylhydrazino) silanes", "Zhurnal Obshceii Khimii", 1960, pp. 694-695, vol. 30.

Sergeeva, Z., et al., "Chemical Abstract 1963:27415, a new method of synthesis of organosilicon hydrazines", "Zhurnal Obshchei Khimii", 1962, pp. 1987-1993, vol. 32.

Sergeeva, Z., et al., "Chemical Abstract 1963:455161, Reaction of nonsymmetric dialkylhydrazines with alkylchloro-silanes", "Zhurnal Obshchei Khimii", 1963, pp. 1874-1878, vol. 33, No. 6.

Smirnova, T., et al., "Plasma-enhanced chemical vapor deposition of silicon carbonitride films from volatile silyl derivatives of 1,1-Dimethylhydrazine", "High Energy Chemistry", Sep. 16-21, 2002, pp. 303-309 (2003), vol. 37, No. 5, Publisher: Proceedings of the 3rd International Symposium on Theoretical and Applied Plasma Chemistry, Ples, Russia.

Smirnova, T., et al., "SiCN alloys obtained by remote plasma chemical vapour deposition from novel precursors", "Thin Solid Films", Apr. 1, 2003, pp. 144-151, vol. 429, No. 1-2.

Smirnova, T., et al., "Composition and Structure of films deposited from silyl derivatives of assymetrical dimthylhydrazine", "Inorganic Materials", Feb. 2003, pp. 117-122, vol. 39, No. 2.

Smirnova, T., et al., "Microstructure and Chemical Bonding in Silicon Carbonitride Films Synthesized by Plasma Enhanced Chemical Vapor Deposition", "Journal of Structural Chemistry", Jan. 2003, pp. 169-173, vol. 44, No. 1.

Soeldner, M., et al., "1,2-Disilanediyl Bis(triflate), F3CSO3—SiH2SiH2—O35CF3, as the Key Intermediate for a Facile Preparation of Open-Chain and Cyclic 1,1- and 1,2-Diaminodisilanes", "Inorg. Chem.", Apr. 23, 1997, pp. 1758-1763, vol. 36, No. 9.

Voronkov, M., et al., "Silyl derivatives Unsymmetrical dimethylhydrazine as Reagents for Synthesis of Composite Structures in Layers in Silicon", "Materialy Elektronnoi Tekhniki (Month of Publication Not Currently Determinable)", 2002, pp. 57-60 (Machine Translation English Abstract), vol. 4.

Wan, Y., et al., "Synthesis of (dialkylamino)disilanes", "Inorg. Chem.", Feb. 3, 1993, pp. 341-344, vol. 32, No. 3.

Wannagat, U., et al., "Chemical Abstract 1959:93473, Hydrazine-silicon compounds II Mixed alkyl-or aryl-substituted hydrazines", "Z. anorg. u allgem. Chem.", 1959, pp. 341-348, vol. 299.

Wannagat, U., et al., "Chemical Abstract 1966:104351, Si—N compounds. LIII. Si—N2H4 compounds. 7. Some new hyrdazinosilanes", "Monatshefte fuer Chemie", 1965, pp. 1902-1908, vol. 96, No. 6.

Wannagat, U., et al., "Chemical Abstract 1967:18737, Silicon-Nitrogen compounds. LXI. Silicaon-hydrazine compounds. 11. Hypergolity of silylhydrazines", "Monatshefte fuer Chemie", 1966, pp. 1157-1162, vol. 97, No. 4.

West, R., et al., "Tetramesityldisilene, a Stable Compound Containing a Silicon-Silicon Double Bond", "Science", Dec. 18, 1981, pp. 1343-1344, vol. 214, No. 4527.

West, R., et al., "Stable silylenes: Synthesis, structure, reactions", "Pure & Appl. Chem.", 1996, pp. 785-788, vol. 68, No. 4.

West, R., et al., "Chemical Shift Tensors and NICS Calculations for Stable Silylenes", "J. Am. Chem. Soc.", Feb. 5, 1998, pp. 1639-1640, vol. 120, No. 7.

Wikipedia Entry for the term 'Vapor Pressure', http://en.wikipedia.org/wiki/Vapor_pressure (Accessed on Jul. 17, 2007.

Witte-Abel, H., et al., "Kondensationen von Silylhydrazinen und Estern zu Silylhydrazonen und Pyrazolnen", "J. Organometallic Chem.", Aug. 15, 1999, pp. 341-347 (English Abstract), vol. 585, No. 2.

Yang, J., et al., "Disilane-Catalyzed and Thermally Induced Oligomerizations of Alkynes: A Comparison", "Organometallics", Mar. 6, 2000, pp. 893-900, vol. 19, No. 5.

Yang, J., et al., "Synthesis of 1,4-disilacyclohexa-2,5-dienes", "Journal of Organometallic Chemistry", Apr. 22, 2002, pp. 276-288, vol. 649.

\* cited by examiner

COMPOSITION AND METHOD FOR LOW TEMPERATURE CHEMICAL VAPOR DEPOSITION OF SILICON-CONTAINING FILMS INCLUDING SILICON CARBONITRIDE AND SILICON OXYCARBONITRIDE FILMS

CROSS REFERENCE TO RELATED APPLICATIONS

This application is a continuation under 35 USC 120 of U.S. patent application Ser. No. 14/333,536, filed Jul. 17, 2014, which is a continuation under 35 USC 120 of U.S. patent application Ser. No. 12/862,739, filed Aug. 24, 2010, issued as U.S. Pat. No. 8,802,882 on Aug. 12, 2014, which is a continuation under 35 USC 120 of U.S. patent application Ser. No. 12/578,262, filed on Oct. 13, 2009, issued as U.S. Pat. No. 7,781,605 on Aug. 24, 2010, which is a continuation under 35 USC 120 of U.S. patent application Ser. No. 10/870,106 entitled "Composition and Method for Low Temperature Chemical Vapor Deposition of the Silicon-Containing Films Including Silicon Carbonitride and Silicon Oxycarbonitride Films," filed on Jun. 17, 2004 in the names of Ziyun Wang, Chongying Xu, Bryan Hendrix, Jeffrey Roeder, Tianniu Chen and Thomas H. Baum, issued Oct. 13, 2009 as U.S. Pat. No. 7,601,860, which in turn is a continuation-in-part under 35 USC 120 of U.S. patent application Ser. No. 10/683,501 entitled "Monosilane or Disilane Derivatives and Method for Low Temperature Deposition of Silicon-Containing Films Using the Same," filed on Oct. 10, 2003 in the names of Ziyun Wang, Chongying Xu and Thomas H. Baum, and issued Aug. 25, 2009 as U.S. Pat. No. 7,579,496. The disclosures of each of these patent applications are hereby incorporated herein by reference in their respective entireties, for all purposes.

FIELD OF THE INVENTION

The present invention relates generally to novel silicon-containing precursors and the formation of silicon-containing films using said precursors in the manufacture of semiconductor devices. More specifically, the present invention relates to silicon-containing precursors and methods for forming silicon-containing films, e.g., films including silicon carbonitride and silicon oxycarbonitride, on a substrate using low temperature (T<550° C.) chemical vapor deposition (CVD) processes.

DESCRIPTION OF THE RELATED ART

In semiconductor manufacturing, thin (e.g., <1,000 nanometers thickness) passive layers of chemically inert dielectric materials, such as silicon nitride ($Si_3N_4$), siliconoxynitride ($SiO_xN_y$) and/or silicon dioxide ($SiO_2$), are widely employed in microelectronic device structures, to function as structural elements of the multi-layered structure, such as sidewall spacer elements, diffusion masks, oxidation barriers, trench isolation coatings, inter-metallic dielectric materials, passivation layers and etch-stop layers.

Recently studies have shown that carbon incorporation (10-15%) in silicon nitride films is beneficial to film quality for transistor sidewall spacer applications. Etch stop and capping layers situated between low dielectric constant (low-k) layers also benefit from a mixture of carbon with silicon nitride or silicon oxide. In addition, pre-metal dielectric (PMD)-liners of silicon nitride require etch selectivity and diffusion barrier properties, which can be enhanced by carbon incorporation into the silicon nitride.

Silicon carbonitride (Si—C—N), which displays the properties of silicon nitride and silicon carbide, is both temperature and oxidation resistant. As such, Si—C—N material is being investigated for use as a hard mask, etch stop or a passivation layer for the Cu dual damascene process.

Si—C—N layers are generally grown using various plasma-enhanced chemical deposition techniques (PECVD).

Deposition of silicon-containing films by CVD techniques is a highly attractive methodology for forming such Si—C—N films. Towards that end, mixtures of monosilane, hydrocarbons, and ammonia or nitrogen have generally been used to synthesize Si—C—N films using CVD at elevated temperatures (T~1300 K). For example, crystalline thin films of Si—C—N have been grown by microwave plasma enhanced CVD (PECVD) at temperatures above 800° C. using a mixture of $H_2$, $CH_4$, $N_2$ and $SiH_4$ gases. However, these mixtures tend to be explosive and flammable. (see, Chen, L. C., et al., *Applied Physics Letters*, 72, 2463-2465 (1998)). More recently, Si—C—N films have been deposited using PECVD at 350° C. to 400° C. using a mixture of trimethylsilane (3MS), helium and ammonia (see, Foresight, April 2003, publication of Applied Materials Taiwan). This disclosed deposition requires high plasma densities that can damage device structures if used in the "front end," e.g., the PMD-liner.

To be compatible with the next generation IC device manufacturing, sidewall spacers need to be deposited by thermal CVD processes at low deposition temperatures, e.g., temperatures less than about 550° C., preferably about 530° C. Because of stringent conformality requirements and proximity to the transistor channel, the use of plasmas is not permitted. Presently used precursors, such as BTBAS, require very high precursor flow rates and have extremely low deposition rates at these temperatures, leading to very high processing costs. Thus, there is a significant need for suitable precursor compositions for such thermal deposition processes. Of particular interest are volatile organosilicon precursors containing appropriate ratios of silicon, nitrogen and carbon.

In addition, to be compatible with the next generation IC device manufacturing, PMD-liners need to be deposited at temperatures less than about 450° C., preferably about 400° C. For this application, low energy density plasmas would be acceptable. Further, etch stop and capping layers to be integrated with low k dielectrics and copper wiring need to be deposited at temperatures below about 400° C., preferably below about 350° C. These layers need to have high structural integrity, good barrier properties with respect to copper diffusion, and a dielectric constant significantly less than that of silicon nitride. For etch stop and capping layers application, PECVD is also acceptable. Again, volatile organosilicon precursors containing appropriate ratios of silicon, nitrogen and carbon are preferable.

Previously, we demonstrated that disilane precursors can offer high deposition rates at low temperatures. For example, silicon nitride films may be deposited at a rate of 26 Å/min by CVD at 450° C. using a mixture of hexaethylamidodisilane (HEADS) precursor and ammonia. Without being bound by theory, the high growth rate is attributed to the weak silicon-silicon bond in the disilane compound, which has a bond energy of 222 kJ/mol. In addition, it has been reported that higher temperatures induce lower deposition rates at the substrate because the reactant desorbs from the surface with the increase in temperature. Notably, disilane ($Si_2H_6$) and hexachlorodisilane (HCDS) ($Si_2Cl_6$), which have the weak Si-Si bond, also have been considered as promising precursors, however, they provide no source of carbon atoms. Further, chlorine may be incorporated into the fabricated chips, which could significantly reduce the chips long-term performance.

The art therefore has a continuing need for improved organosilicon precursors for forming silicon-containing films, such as low k silicon-containing thin films including silicon oxynitride, silicon nitride, silicon carbonitride and silicon oxycarbonitride.

SUMMARY OF THE INVENTION

The present invention relates generally to the formation of silicon-containing films in the manufacture of semiconductor devices, and more specifically to novel silicon precursors and methods for forming silicon-containing films, such as silicon-containing low k films and films comprising silicon carbonitride (Si—C—N), and silicon oxycarbonitride (Si—O—C—N), on a substrate using low temperature (T<550° C.) CVD processes.

The present invention in one aspect relates to a silicon compound selected from the group consisting of:
(A) compounds of the formula:

$$(R^2R^3N)_{3-x}R^1_xSi\text{—}SiR^1_x(NR^2R^3)_{3-x}$$

wherein:

$R^1$, $R^2$, and $R^3$ may be the same as or different from one another and each is independently selected from the group consisting of H, $C_1$-$C_5$ alkyl, $C_3$-$C_6$ cycloalkyl, aryl, arylalkyl; and x is 1 or 2);
(B) compounds of the formula:

$$\begin{array}{c} R^1 \quad\quad R^3 \quad X \\ \diagdown \quad\; | \quad\;\; | \\ N\text{—}N\text{—}Si\text{—}Y \\ \diagup \quad\quad\quad | \\ R^2 \quad\quad\quad Z \end{array}$$

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and X, Y, and Z may be the same as or different from the other and each is independently selected from the group consisting of H, alkyl, alkylamino, dialkylamino and alkylhydrazido;

with the proviso that when $R^1$, $R^2$, X and Y are methyl groups and $R^3$ is hydrogen, Z cannot be hydrogen; and
(C) compounds of the formula:

$$\begin{array}{c} R^1 \quad\quad R^3 \quad X^1 \quad X^2 \quad R^3 \quad\quad R^1 \\ \diagdown \quad\; | \quad\;\; | \quad\;\; | \quad\;\; | \quad\;\; \diagup \\ N\text{—}N\text{—}Si\text{—}Si\text{—}N\text{—}N \\ \diagup \quad\quad\quad | \quad\;\; | \quad\quad\quad \diagdown \\ R^2 \quad\quad\quad Y^1 \quad Y^2 \quad\quad\quad R^2 \end{array}$$

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and $X^1$, $X^2$, $Y^1$, $Y^2$, $Z^1$ and $Z^2$ may be the same as or different from the other and each is independently selected from the group consisting of H, alkyl, alkylamino, dialkylamino and alkylhydrazido.

Another aspect of the present invention relates to a method of forming a silicon-containing film on a substrate, comprising contacting a substrate under chemical vapor deposition conditions, at a temperature below 600° C., with a vapor of a silicon compound selected from the group consisting of:
(A) compounds of the formula:

$$(R^2R^3N)_{3-x}R^1_xSi\text{—}SiR^1_x(NR^2R^3)_{3-x}$$

wherein:

$R^1$, $R^2$, and $R^3$ may be the same as or different from one another and each is independently selected from the group consisting of H, $C_1$-$C_5$ alkyl, $C_3$-$C_6$ cycloalkyl, aryl, arylalkyl; and x is 1 or 2;
(B) compounds of the formula:

$$\begin{array}{c} R^1 \quad\quad R^3 \quad X \\ \diagdown \quad\; | \quad\;\; | \\ N\text{—}N\text{—}Si\text{—}Y \\ \diagup \quad\quad\quad | \\ R^2 \quad\quad\quad Z \end{array}$$

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and X, Y, and Z may be the same as or different from the other and each is independently selected from the group consisting of H, alkyl, alkylamino, dialkylamino and alkylhydrazido;

with the proviso that when $R^1$, $R^2$, X and Y are methyl groups and $R^3$ is hydrogen, Z cannot be hydrogen;
(C) compounds of the formula:

$$\begin{array}{c} R^1 \quad\quad R^3 \quad X^1 \quad X^2 \quad R^3 \quad\quad R^1 \\ \diagdown \quad\; | \quad\;\; | \quad\;\; | \quad\;\; | \quad\;\; \diagup \\ N\text{—}N\text{—}Si\text{—}Si\text{—}N\text{—}N \\ \diagup \quad\quad\quad | \quad\;\; | \quad\quad\quad \diagdown \\ R^2 \quad\quad\quad Y^1 \quad Y^2 \quad\quad\quad R^2 \end{array}$$

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and $X^1$, $X^2$, $Y^1$, $Y^2$, $Z^1$ and $Z^2$ may be the same as or different from the other and each is independently selected from the group consisting of H, alkyl, alkylamino, dialkylamino and alkylhydrazido; and
(D) compounds of the formula:

$$(R^1R^2N)_2Si\!:, \quad\quad\quad\quad\quad\quad\quad\quad\quad\quad\quad\quad\quad (i)$$

$$(R^1R^2N)_2Si\!=\!Si(NR^1R^2)_2, \text{ and} \quad\quad\quad\quad\quad (ii)$$

$$(R^1R^2N)_2HSi\text{—}SiR^3_nH_{3-n}, \quad\quad\quad\quad\quad\quad\quad (iii)$$

wherein $R^1$, $R^2$ and $R^3$ may be the same as or different from the other and each is independently selected from the group consisting of H, $C_1$-$C_4$ alkyl, amino, silyl groups (—$SiH_3$) and hydrocarbyl derivatives of silyl groups (e.g., —$SiR_3$); and $0 \leq n \leq 3$.

Yet another aspect of the present invention relates to a method of making a silicon compound of the formula $$(R^2R^3N)_{3-x}R^1_xSi\text{—}SiR^1_x(NR^2R^3)_{3-x}$$

wherein:

$R^1$, $R^2$, and $R^3$ may be the same as or different from one another and each is independently selected from the group consisting of H, $C_1$-$C_5$ alkyl, $C_3$-$C_6$ cycloalkyl, aryl, arylalkyl; and x is 1 or 2;

said method comprising reacting a disilane compound of the formula $XR^1R^2Si-SiXR^1R^2$ with a secondary amine ($R^2R^3NH$) and a tertiary amine ($R^1R^2R^3N$) compound, wherein X is selected from the group consisting of bromine, fluorine and chlorine, and $R^1$, $R^2$ and $R^3$ are as set out above, according to the following reaction:

$$XR^1R^2Si-SiXR^1R^2+R^2R^3NH+R^1R^2R^3N \rightarrow \\ (R2R3N)_{3-x}R^1{}_xSi-SiR^1{}_x(NR2R3)_{3-x}$$

Other aspects, features and embodiments of the invention will be more fully apparent from the ensuing disclosure and appended claims.

DETAILED DESCRIPTION OF THE INVENTION AND PREFERRED EMBODIMENTS THEREOF

Figure 1:
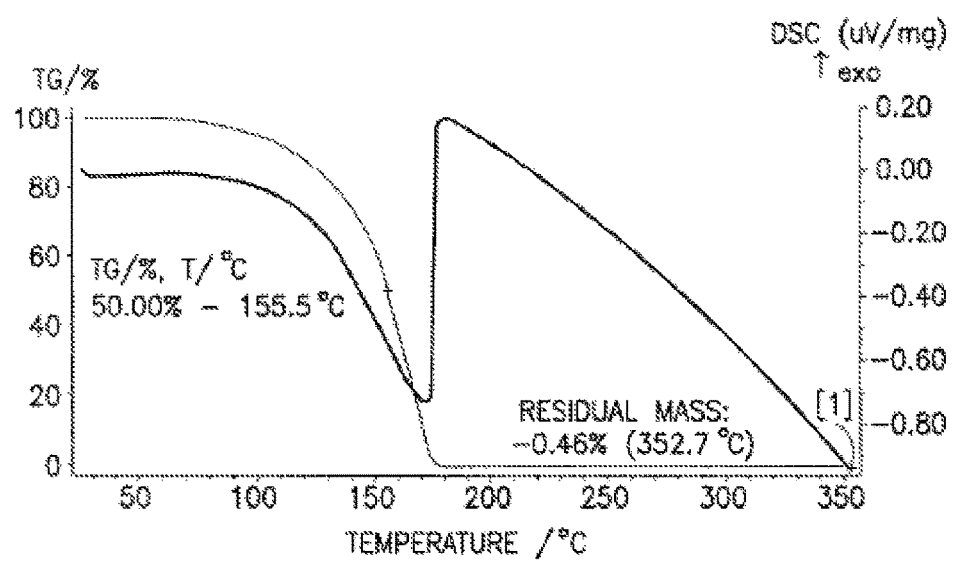
FIG. 1 is an STA plot for $Me_2(NEt_2)Si-Si(NEt_2)Me_2$ in Ar.

The present invention relates to novel silicon precursors for the CVD formation of silicon carbonitride and/or silicon oxycarbonitride films on substrates at low temperatures, and to corresponding processes for forming such films with such precursors.

In one aspect, the invention provides a compound of the formula:

$$(R^2R^3N)_{3-x}R^1{}_xSi-SiR^1{}_x(NR^2R^3)_{3-x} \qquad (1)$$

wherein:

$R^1$, $R^2$, and $R^3$ may be the same as or different from one another and each is independently selected from the group consisting of H, $C_1$-$C_5$ alkyl, $C_3$-$C_6$ cycloalkyl, aryl, arylalkyl; and x is 1 or 2.

The compounds of formula (1) are usefully employed for forming silicon-containing films by chemical vapor deposition, utilizing process conditions including a deposition temperature of less than 600° C., more preferably less than 550° C., and appertaining pressures, concentrations, flow rates and CVD techniques, as readily determinable within the skill of the art for a given application, based on the disclosure herein.

"Silicon-containing films" are defined herein means silicon nitride, silicon oxynitride, silicon carbonitride, silicon oxycarbonitride, low-k thin silicon-containing films, high-k gate silicate films and low temperature silicon epitaxial films.

Preferred compounds of formula (1) include $Me_2(NEt_2)Si-Si(NEt_2)Me_2$, $Me_2(NEtMe)Si-Si(NEtMe)Me_2$, and $Me_2(NMe_2)Si-Si(NMe_2)Me_2$.

Compounds of formula (1) are readily synthesized by reaction of disilane compounds of the formula $R^1{}_2XSi-SiXR^1{}_2$ with a secondary amine ($R^2R^3NH$) and a tertiary amine ($R^1R^2R^3N$) compound, wherein X is selected from the group consisting of bromine, fluorine and chlorine, and $R^1$, $R^2$ and $R^3$ are as set out above. For example, $Me_2(NEt_2)Si-Si(NEt_2)Me_2$ can be prepared according to the following reaction:

$$Me_4Si_2Cl_2+2NEt_3+2HNEt_2 \rightarrow Me_4Si_2(NEt_2)_2+2NEt_3 \cdot HCl$$

as hereinafter more fully described in the examples herein.

The invention in another aspect relates to a group of halogen-free silanes or disilane derivatives that are substituted with at least one alkylhydrazine functional group and can be used as CVD precursors for deposition of silicon-containing thin films.

The silane derivatives of the present invention can be represented by the general formula:

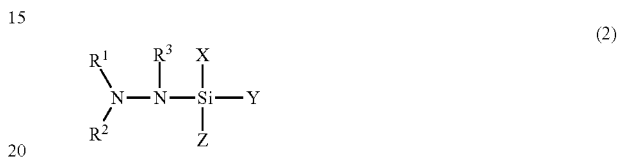

(2)

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and X, Y, and Z may be the same as or different from the other and each is independently selected from the group consisting of H, alkyl, alkylamino, dialkylamino and alkylhydrazido (e.g., $R^1R^2NNH-$, wherein $R^1$ and $R^2$ are the same as described hereinabove);

with the proviso that when $R^1$, $R^2$, X and Y are methyl groups and $R^3$ is hydrogen, Z cannot be hydrogen.

The silane derivatives of the present invention can also be represented by the general formula:

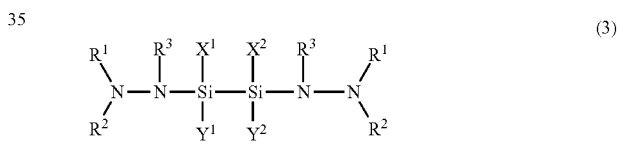

(3)

wherein $R^1$, $R^2$ and $R^3$ may be the same as or different from the other and each is independently selected from the group consisting of H, $C_1$-$C_5$ alkyl, $C_3$-$C_6$ cycloalkyl, aryl and arylalkyl; and $X^1$, $X^2$, $Y^1$, $Y^2$, $Z^1$ and $Z^2$ may be the same as or different from the other and each is independently selected from the group consisting of H, alkyl, alkylamino, dialkylamino and alkylhydrazido.

Preferably, the disilane derivative compounds of the present invention are characterized by functional groups that are symmetrically distributed in relation to the Si-Si bond.

Compounds of formula (2) and (3) are readily synthesized by reaction of disilane compounds of the formula $R^1{}_2XSi-SiXR^1{}_2$ with an amine ($R^1R^2R^3N$) compound and a hydrazine compound ($H_2NNR^1{}_2$), wherein X is selected from the group consisting of bromine, fluorine and chlorine, and $R^1$, $R^2$ and $R^3$ are as set out above. For example, $Me_2(Me_2NNH)Si-Si(NHNMe_2)Me_2$ can be prepared according to the following reaction:

$$Me_4Si_2Cl_2+2NEt_3+2H_2NNMe_2 \rightarrow \\ Me_4Si_2(NHNMe_2)_2+2NEt_3 \cdot HCl$$

as hereinafter more fully described in the examples herein.

The compounds of formulas (2) and (3) are usefully employed for forming silicon-containing films by chemical vapor deposition, utilizing process conditions including a deposition temperature of less than 600° C., more preferably less than 550° C., and appertaining pressures, concentrations, flow rates and CVD techniques, as readily determinable within the skill of the art for a given application, based on the disclosure herein.

Another class of silicon-containing precursors in accordance with the invention, which are amenable to CVD processes at low temperatures, such as in the range of from about 350° C. to about 550° C., for pre- and post-metal deposition of thin (e.g., 500 Angstroms to 1 micrometer thickness) dielectric films of silicon nitride or silicon oxynitride in semiconductor manufacturing, or otherwise for forming silicon nitride or silicon oxynitride ceramic thin films on different substrates, include the diaminosilylenes of formula (4) and their derivatives thereof, represented by formulae (5) and (6):

  (4)

  (5)

  (6)

wherein $R^1$, $R^2$ and $R^3$ may be the same as or different from the other and each is independently selected from the group consisting of H, $C_1$-$C_4$ alkyl, amino, silyl groups ($—SiH_3$) and hydrocarbyl derivatives of silyl groups (e.g., $—SiR_3$); and
$0 \leq n \leq 3$.

Diamino-silylenes as represented by formula (4) are diradical species, some of which are not stable and easily form the derivatives as represented in formulae (5) and (6), while others are remarkably stable and can be readily delivered in their diradical form.

An exemplary stable silylene compound includes the following diaminosilylene:

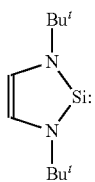

This diaminosilylene remains unchanged after boiling in toluene at 150° C. for four months. Thermal decomposition takes place at 220° C. The stability of this diaminosilylene is thought to result in part from aromatic stabilization (see, Denk, M., et al., *J. Am. Chem. Soc.*, 116, 2691-2692 (1994).

Diaminosilylenes represented by formula (4) can be synthesized according to the following mechanism (see, West, R., Denk, M., *Pure Appl. Chem.*, 68, 785-788 (1996)):

The compounds of formulae (5) and (6) can be made in accordance with the reaction scheme shown below:

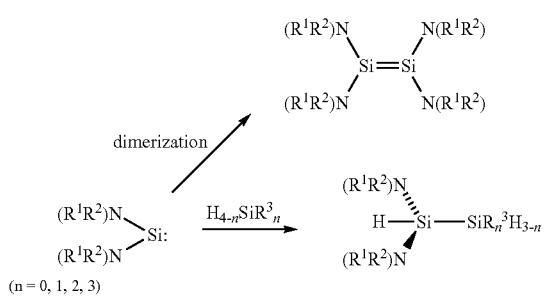

(n = 0, 1, 2, 3)

In accordance with teaching herein, the type of dielectric film produced by the corresponding CVD process can be tailored by choice of the specific silicon-containing precursor of formulae (1)-(6). For example, ammonia, oxygen or nitric oxide may be used as alternative single reactants to form the respective silicon nitride, silicon oxynitride, silicon carbonitride and/or silicon oxycarbonitride single component films, or a mixture of two or more of such reactants can be employed in the CVD process with selected one(s) of the formulae (1)-(6) precursors to form corresponding multi-component films, or graded composition films. Alternatively, mono-, di- and trialkyl amines, of the formula $R^1R^2R^3N$ may be employed as reactants, wherein $R^1$, $R^2$ and $R^3$ may be the same as or different from the other and each is independently selected from the group consisting of H, and $C_1$-$C_4$ alkyl groups. In addition, inert carrier gases may be present in the precursor gas, including helium, argon and nitrogen.

In application, the silicon-containing precursor is reacted with a desired co-reactant in any suitable manner, e.g., in a single wafer CVD chamber, or in a furnace containing multiple wafers, utilizing process conditions including a deposition temperature of less than 600° C., more preferably less than <550° C., and appertaining pressures, concentrations, flow rates and CVD techniques, as readily determinable within the skill of the art for a given application, based on the disclosure herein. For example, when depositing sidewall spacers, PMD liners, or etch-stop and capping layers, temperatures of less than 550° C., less than 450° C., and less than 400° C., respectively, should be used. With respect to pressure, deposition pressures may range from about 1 Ton to about 80 Torr.

The features and advantages of the invention are more fully shown by the following illustrative and non-limiting examples.

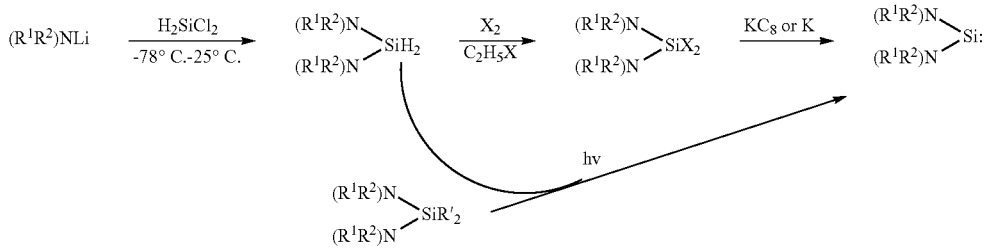

EXAMPLE 1

Synthesis of Me$_2$(NEt$_2$)Si—Si(NEt$_2$)Me$_2$

In a 1 L flask, 300 mL of hexanes and 350 mL (1.6 M, 560 mmol) of n-butyllithium in hexanes were mixed. To this solution, 41 g of HNEt$_2$ (560 mmol) was added at 0° C. White precipitate material was observed immediately. Upon completion of the addition, the reaction flask was allowed to warm to room temperature and stirred for an additional hour. Then, 50 g of Me$_4$Si$_2$Cl$_2$ (270 mmol) in 100 mL of diethyl ether was slowly added to the flask at room temperature. The mixture was stirred overnight and filtered at room temperature. The crude product, 59 g (227 mmol) 85% yield, was obtained after removal of the volatiles from the filtrate. The pure product was obtained by vacuum distillation (b.p. ~62° C. at 190 mTorr). $^1$H NMR (C$_6$D$_6$): 0.26 (s, 12 H, —CH$_3$Si); 1.00 (t, 12 H, —CH$_3$CH$_2$N); 2.83 (q, 8H, —CH$_3$CH$_2$N). $^{13}$C{$^1$H} NMR (C$_6$D$_6$): δ0.33 (—CH$_3$Si); 16.2 (—NCH$_2$CH$_3$); 41.3 (—NCH$_2$CH$_3$). Mass spectrum: m/z 260 [M+]; 188 [M+-(—NEt$_2$)]; 130 [M+-(—SiMe$_2$(NEt$_2$)]. C$_{12}$H$_{32}$N$_2$Si$_2$: Found (theory), C: 54.98% (55.31%), H: 12.41% (12.38%), N: 10.66% (10.75%).

FIG. 1 shows that the STA data indicates that the T$_{50}$ value of Me$_2$(NEt$_2$)Si—Si(NEt$_2$)Me$_2$ is about 160° C., evidencing good volatility and transport properties for chemical vapor deposition.

EXAMPLE 2

Synthesis of Me$_2$(Me$_2$NNH)Si—Si(NHNMe$_2$)Me$_2$

A 3 L flask was filled with a solution comprising 2.5 L of hexanes, 50 grams (267 mmol) of Me$_4$Si$_2$Cl$_2$, and 57 grams (561 mmol) of anhydrous NEt$_3$. 34 grams of H$_2$NNMe$_2$ (561 mmol), dissolved in 100 mL of diethyl ether, was slowly added to the flask at room temperature. White precipitate was observed during the addition of H$_2$NNMe$_2$ to the solution. Following completion of the addition, the mixture was stirred overnight, filtered, and all volatile materials were removed from the filtrate under vacuum. The crude yield was 86% (54 g, 230 mmol). Vacuum distillation was used to purify the end product, which has a boiling point of approximately 45° C. at 35 mTorr. $^1$H NMR (C$_6$D$_6$): δ0.33 (s, 12H, —CH$_3$Si), 1.90 (br, 2H, —HN), 2.27 (s, 12H, —CH$_3$N). $^{13}$C{$^1$H} NMR (C$_6$D$_6$): δ-0.68 (—SiCH$_3$), 52.6 (—NCH$_3$). Mass spectrum: m/z 175 [M$^+$-(—HNNMe$_2$)], 132 [M$^+$-(—HNNMe$_2$)-(—NMe$_2$)], 116 [M$^+$-(—SiMe$_2$(HNNMe$_2$)]. C$_8$H$_{26}$N$_4$Si$_2$: Found (calculated) C: 40.81% (40.98%), H: 10.99% (11.18%), and N: 23.67% (23.89%).

Figure 2:
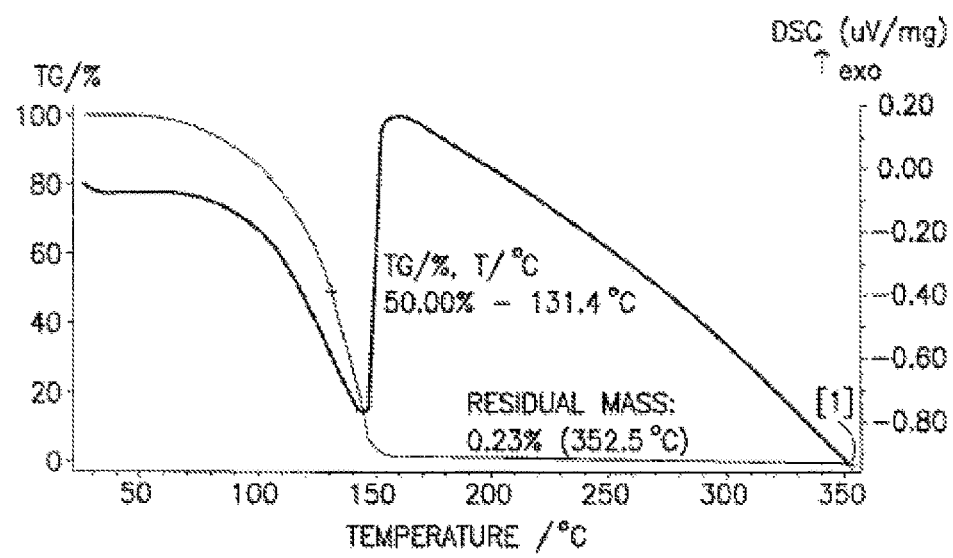
FIG. 2 is an STA plot for $Me_4Si_2(NHNMe_2)_2$ in Ar.

FIG. 2 shows the STA plot for Me$_4$Si$_2$(NHNMe$_2$)$_2$, which is a liquid at room temperature and can be transported in its vapor form completely with very little (<1%) residual material at about 350° C. The thermal stability of Me$_4$Si$_2$(HNNMe$_2$)$_2$ in solution at 100° C. was monitored by proton NMR study for 7 days, and no significant decomposition was detected.

EXAMPLE 3

Silicon Carbonitride Deposition from Me$_4$Si$_2$(NHNMe$_2$)$_2$

A solution of the compound of Example 2, Me$_4$Si$_2$(NHNMe$_2$)$_2$, was prepared at a concentration of 0.40M in a hydrocarbon solvent. This solution was metered at 0.10 mL per minute (equivalent to about 2 sccm) with 10 sccm of He as a carrier gas and vaporized at 70° C. The vapor was mixed with 10 sccm of NH$_3$ in a showerhead device that was maintained at 100° C. and thereby dispersed over the surface of a Si(100) wafer heated to 550° C. The chamber pressure was maintained at 1 Torr during deposition. The film was deposited at a rate of 1.3 nm/minute.

Hydrocarbon solvents contemplated herein for use as precursor solvents include, but are not limited to, alkanes, alkenes, alkynes, cycloalkanes, aromatic compounds such as benzene and its derivatives thereof, alkanols and amines.

Chemical analysis of the film, using a combination of RBS (Rutherford Backscattering), HFS (Hydrogen Forward Scattering), and NRA (Nuclear Reaction Analysis) techniques, revealed that the film composition was 22.9% Si, 13.2% N, 33.1% C, 25.0% H and the index of refraction at 632 nm was 1.98.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A silicon compound of the formula:

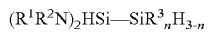

(R$^1$R$^2$N)$_2$HSi—SiR$^3_n$H$_{3-n}$ wherein R$^1$, R$^2$ and R$^3$ may be the same as or different from each other and each is independently selected from the group consisting of H, C$_1$-C$_4$ alkyl, amino, silyl groups (-SiH$_3$) and hydrocarbyl derivatives of silyl groups; and 0≤n≤3.

2. The silicon compound of claim 1, wherein R$^1$, R$^2$ and R$^3$ may be the same as or different from each other and each is independently a hydrocarbyl derivative of a silyl group.

3. The silicon compound of claim 1, wherein R$^1$, R$^2$ and R$^3$ are the same.

4. The silicon compound of claim 3, wherein R$^1$, R$^2$ and R$^3$ are selected from C$_1$-C$_4$ alkyl.

5. The silicon compound of claim 1, wherein R$^1$, R$^2$ and R$^3$ may be the same as or different from each other and each is independently selected from the group consisting of H and C$_1$-C$_4$ alkyl.

6. The silicon compound of claim 1, wherein R$^1$, R$^2$ or R$^3$ is a silyl group.

7. The silicon compound of claim 1, wherein R$^1$, R$^2$ and R$^3$ may be the same as or different from each other and each is independently a silyl group or a hydrocarbyl derivative of a silyl group.

8. A composition comprising a silicon compound of the formula:

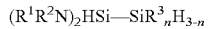

(R$^1$R$^2$N)$_2$HSi—SiR$^3_n$H$_{3-n}$ wherein R$^1$, R$^2$ and R$^3$ may be the same as or different from each other and each is independently selected from the group consisting of H, C$_1$-C$_4$ alkyl, amino, silyl groups (-SiH$_3$) and hydrocarbyl derivatives of silyl groups; and 0≤n≤3, and wherein said silicon compound is in a vapor form.

9. The composition of claim 8, further comprising an inert carrier gas.

10. The composition of claim 9, wherein said inert carrier gas is selected from among helium, argon and nitrogen.

11. The composition of claim 8, further comprising a co-reactant.

12. The composition of claim 11, wherein the co-reactant is selected from among ammonia, oxygen, nitric oxide, monoalkylamines, dialkylamines, and trialkyl amines, and mixtures of two or more thereof.

13. The composition of claim 8, further comprising a solvent.

14. The composition of claim 13, wherein the solvent comprises a hydrocarbon solvent.

15. The composition of claim 14, wherein the hydrocarbon solvent comprises a solvent selected from the group consisting of alkanes, alkenes, alkynes, cycloalkanes, aromatic compounds, benzene, benzene derivatives, alkanols and amines.

16. A method of forming a silicon-containing film on a substrate, comprising contacting a substrate under chemical vapor deposition conditions, at a temperature below 600° C., with a vapor of a silicon compound of the formula:

$$(R^1R^2N)_2HSi\text{—}SiR^3{}_nH_{3-n}$$

wherein $R^1$, $R^2$ and $R^3$ may be the same as or different from each other and each is independently selected from the group consisting of H, $C_1$-$C_4$ alkyl, amino, silyl groups (-$SiH_3$) and hydrocarbyl derivatives of silyl groups; and $0 \leq n \leq 3$.

17. The method of claim 16, wherein $R^1$, $R^2$ and $R^3$ are selected from the group consisting of $C_1$-$C_4$ alkyl.

18. The method of claim 16, wherein the temperature is below 550° C.

19. The method of claim 16, wherein the vapor further comprises a co-reactant.

20. The method of claim 19, wherein the co-reactant is selected from among ammonia, oxygen, nitric oxide, monoalkylamines, dialkylamines, and trialkyl amines, and mixtures of two or more thereof.

* * * * *